(12) United States Patent
Buurman et al.

(10) Patent No.: US 9,785,742 B2
(45) Date of Patent: Oct. 10, 2017

(54) SEARCH ENGINE FOR MEDICAL DATA

(75) Inventors: Johannes Buurman, 's-Hertogenbosch (NL); Rutger Nijlunsing, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/127,790

(22) PCT Filed: Oct. 29, 2009

(86) PCT No.: PCT/IB2009/054817
§ 371 (c)(1),
(2), (4) Date: May 5, 2011

(87) PCT Pub. No.: WO2010/055432
PCT Pub. Date: May 20, 2010

(65) Prior Publication Data
US 2011/0213774 A1 Sep. 1, 2011

Related U.S. Application Data

(60) Provisional application No. 61/114,551, filed on Nov. 14, 2008.

(51) Int. Cl.
*G06F 7/00* (2006.01)
*G06F 17/30* (2006.01)
*G06F 19/00* (2011.01)

(52) U.S. Cl.
CPC .......... *G06F 19/322* (2013.01); *G06F 19/321* (2013.01)

(58) Field of Classification Search
USPC ........................................................ 707/736
See application file for complete search history.

(56) References Cited

U.S. PATENT DOCUMENTS

| | | | |
|---|---|---|---|
| 5,974,412 A | 10/1999 | Hazlehurst et al. | |
| 6,212,527 B1 | 4/2001 | Gustman | |
| 7,106,890 B1 * | 9/2006 | Grant | G06F 19/321 382/128 |
| 7,953,614 B1 * | 5/2011 | Reicher | G06Q 10/10 705/2 |
| 8,856,175 B2 * | 10/2014 | Marsh | G06F 21/604 707/706 |
| 2002/0052861 A1 | 5/2002 | Gustman | |
| 2003/0125987 A1 * | 7/2003 | Rucker | G06F 19/327 705/3 |
| 2004/0078238 A1 * | 4/2004 | Thomas | G06F 19/321 705/3 |
| 2004/0153965 A1 * | 8/2004 | O'Rourke | G06F 17/243 715/223 |

(Continued)

OTHER PUBLICATIONS

Nadkarni, P. M., et al.; Organization of Heterogeneous Scientific Data Using the EAV/CR Representation; 1999; Jamia; 6(6)478-493.

(Continued)

*Primary Examiner* — Binh V Ho

(57) ABSTRACT

A system having a first data storage element storing a first set of data including patient images and a second data storage element storing a second set of data that is derived from the first set of data, the second set of data including searchable data that is descriptive of the first set of data and excludes the patient images.

18 Claims, 2 Drawing Sheets

(56) References Cited

U.S. PATENT DOCUMENTS

| | | | |
|---|---|---|---|
| 2005/0021512 A1* | 1/2005 | Koenig | G06Q 50/22 |
| 2005/0108060 A1* | 5/2005 | Sasano | G06Q 50/24 |
| | | | 705/3 |
| 2005/0187904 A1* | 8/2005 | Nose | G06F 9/543 |
| 2007/0088695 A1 | 4/2007 | Bleyendaal et al. | |
| 2007/0118540 A1* | 5/2007 | Guo | G06F 17/30265 |
| 2007/0192354 A1* | 8/2007 | Wei | G06F 19/321 |
| 2007/0237377 A1* | 10/2007 | Oosawa | G06F 19/321 |
| | | | 382/128 |
| 2008/0059244 A1* | 3/2008 | Fujita | G06F 19/321 |
| | | | 705/3 |
| 2008/0095418 A1* | 4/2008 | Moriya | A61B 6/563 |
| | | | 382/128 |
| 2009/0022377 A1* | 1/2009 | Matsue | G06F 19/321 |
| | | | 382/128 |
| 2009/0054755 A1* | 2/2009 | Shiibashi | G06F 19/321 |
| | | | 600/407 |
| 2009/0103789 A1* | 4/2009 | Danner | G06F 19/321 |
| | | | 382/128 |
| 2009/0164436 A1* | 6/2009 | Du | G06F 19/321 |
| 2009/0313495 A1* | 12/2009 | Krishnan | G06F 19/321 |
| | | | 713/600 |
| 2010/0098309 A1* | 4/2010 | Graessner | G06K 9/00 |
| | | | 382/131 |
| 2011/0213774 A1 | 9/2011 | Buurman et al. | |

OTHER PUBLICATIONS

Nadkarni, P. M.; Clinical patient record systems architecture: an overview; 2000; E-Medicine; 46(3)199-204.

* cited by examiner

SEARCH ENGINE FOR MEDICAL DATA

BACKGROUND

Existing medical image storage systems typically store images indexed by patient identifiers. Such systems are well suited to searching for images for a particular patient using simple database queries. However, they are not suited to more complicated search criteria and advanced searches, because more detailed information is not available. Medical professionals may wish to be able to perform more advanced searches.

SUMMARY OF THE INVENTION

A system having a first data storage element storing a first set of data including patient images and a second data storage element storing a second set of data that is derived from the first set of data, the second set of data including searchable data that is descriptive of the first set of data and excludes the patient images.

A method for storing a first set of data including patient images, extracting, from the first set of data, searchable data that is descriptive of the first set of data to create a second set of data, the second set of data excluding the patient images and storing the second set of data.

DETAILED DESCRIPTION

Figure 1:
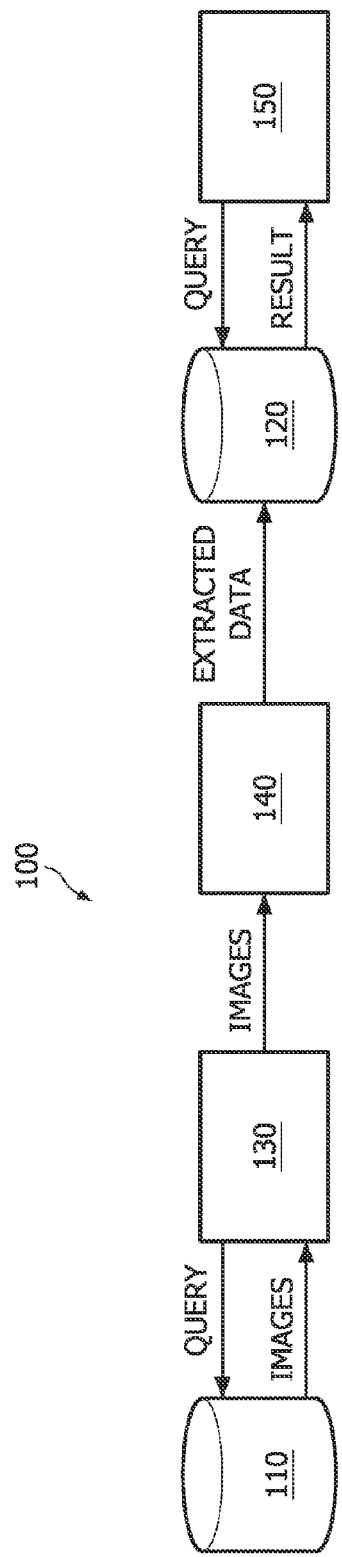
FIG. 1 shows an exemplary system for providing a medical database with enhanced search features.

The exemplary embodiments may be further understood with reference to the following description and the appended drawings, wherein like elements are referred to with the same reference numerals. The exemplary embodiments describe systems and methods for providing databases of medical information that support advanced search queries.

Existing systems for storing patient images, such as Picture Archiving and Communication Systems ("PACS") are typically indexed by patient information. This information may include patient name and birth date, other patient identifiers, or study identifiers. Querying such an index for data using patient or study identifiers is simple and effective; however, searching based on other criteria is difficult or impossible. Therefore, though such databases are useful for some purposes, additional utility can be achieved by adapting existing databases to be queried in newer, more complex ways.

FIG. 1 illustrates an exemplary system 100. The system 100 includes a repository database 110, which stores patient information and is, for example, a PACS database, a pathology information system, etc. As described, the repository database 110 stores patient images indexed by, for example, a patient identifier, a study identifier, or other similar criteria. Typically, such data is stored according to the Digital Imaging and Communications in Medicine ("DICOM") standard. The user's ability to query the database 110 alone is limited as described above. However, the system 100 also includes a search database 120, which is created from the repository database 110 as will be described herein. The format of the search database 120 may be any database that is appropriate for this purpose; it may be as simple as a spreadsheet, but preferably is a database built specifically for this purpose. The system 100 also includes a bot 130 and a filter 140, which are used to create the search database 120.

The bot 130 and the filter 140 are typically software applications that reside on the system 100, although they may be located elsewhere, and may be stored in separate locations from one another. For example, different portions of a hospital may have separate PACS databases or there may be separate PACS databases at a series of affiliated hospitals. The bot 130 and the filter 140 may reside at one of these hospitals or portions of the hospital, but may have access to all the PACS databases. Additionally, the search database 120 may be located remotely from the patient image repository database 110 or may be located at the same location. The operation of these elements will be described in further detail below. The system 100 also includes a search interface 150, which may be part of a clinical application provided so that users may access the search database 120 through a user interface.

Figure 2:
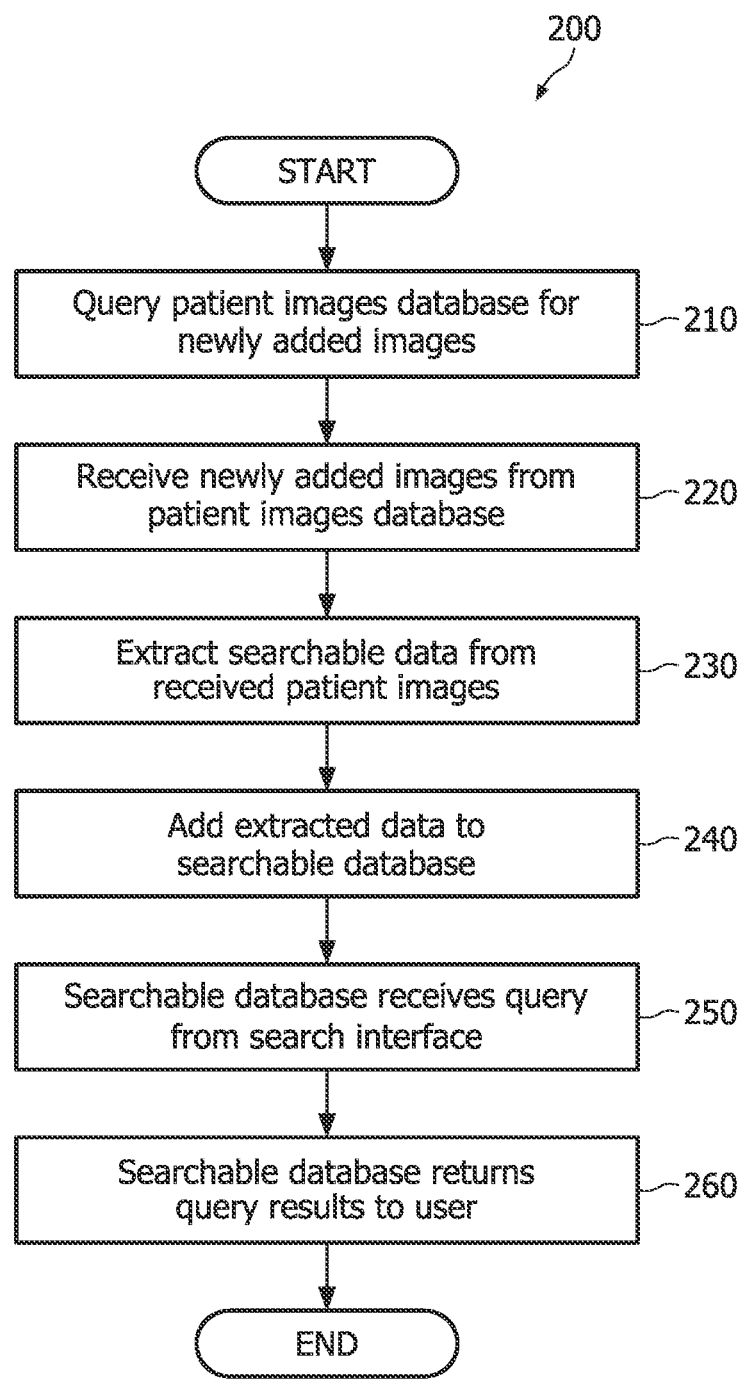
FIG. 2 shows an exemplary method for creating and using a medical database with enhanced search features.

FIG. 2 illustrates an exemplary method 200. The method 200 will be described with reference to the process for constructing the search database 120 from the patient image repository database 110; however, the broader concepts illustrated by the exemplary method 200 are also applicable to systems other than that of FIG. 1. In step 210, the patient image repository database 110 is queried by the bot 130 to determine whether it contains new images that have not yet been indexed in the search database 120. As will be understood, when the search database 120 is being created, an initial query will retrieve all images from the repository database 110; subsequent queries will retrieve at least those images that have been added to the repository database 110 since the most recent previous query, and may be performed at regular intervals (e.g., weekly). In alternative implementations, the query may be structured to retrieve all images from the repository database 110, including those that have recently been added. Preferably, queries are performed during time periods when system and network usage is low, such as overnights or weekends. It should be noted that the bot 130 may automatically query the database 110 based on a schedule or an event, or may be started manually by a user. In step 220, new images are retrieved by the bot 130 from the repository database 110 and passed to the filter 140.

In step 230, the filter 140 processes the images retrieved from the repository database 110 in order to provide searchable information for the search database 120. This processing step includes filtering images stored in the repository database 110 to extract searchable data. The data may be stored in the images (e.g., in a DICOM format) or derivable therefrom. The exact nature of the data to be extracted depends on the purpose for which the search database 120 is to be used; further, the extracted data is typically limited to that data which is relevant to the purpose of the search database 120. Pixel data stored in the images in the repository database 110 is typically removed from the data in order to obtain a search database 120 of a more manageable size; for a repository database 110 storing images in a DICOM format, pixel data may comprise 95% to 99% of the stored data volume. Thus, removal of the pixel data will result in a manageably sized database.

In step 240, the extracted data is added to the searchable search database 120. The first time the method 200 is performed, this step 240 includes the creation of a new searchable search database 120; subsequently, data is added to an existing search database 120. As discussed above, the search database 120 may be of any type suitable for storing this data, but preferably is of a type dedicated to this task.

Thus, at the completion of step 240, the search database 120 is current and can be searched by a user. As described above, the search database 120 will be significantly smaller than the repository database 110 and is also optimized based on the data that is included. That is, as described herein, the exemplary embodiments create smaller databases that have new searchable indexes from the larger database. However, these new searchable indexes are created using existing indices that are previously generated based on knowledge of the field in the original database resulting in an optimized database. Thus, searching the search database 120 becomes faster and easier than searching the repository database 110. Further, many types of searches may be possible using the search database 120 that could not be accomplished at all using solely the repository database 110.

In step 250, the search database 120 is queried by the search interface 150. As described above, the query may take a more detailed form than what would be possible with the patient image repository database 110. For example, a user may search for all mammography structured reports containing more than three findings, or all dynamic contrast-enhanced MRI scans of the prostate with a temporal resolution of better than two seconds. The specific form of the query may vary from embodiment to embodiment, and may take any of various forms depending on the specific information that a user desires. For example, in one embodiment, the query may be text-based; in another, it may use a set of filters.

In step 260, the results of the query of step 250 are provided to the user. This may involve displaying results as a list, in a table, or in various other formats known in the art. Results will typically include references to entries in the patient image repository database 110, which can then be retrieved by the user via methods that are known in the art.

By the implementation of the above exemplary embodiments, users may be able to search for patient information using queries that are more detailed than those possible with existing methods. Further, such searches may utilize multiple search terms in a manner not allowed by existing methods. In addition, since the search database 120 contains only the relevant data (e.g., with image data being removed), faster searches may be performed.

In the above example, the search database 120 contains data for a single image repository database 110. However, it should be understood that the search database 120 may include data from multiple image databases or from other types of databases, allowing a user to search multiple storage locations using a single search database 120.

It will be apparent to those skilled in the art that various modifications may be made, without departing from the spirit or the scope of the invention. Thus, it is intended that the present disclosure cover modifications and variations, provided they come within the scope of the appended claims and their equivalents.

It is also noted that the claims may include reference signs/numerals in accordance with PCT Rule 6.2(b). However, the present claims should not be considered to be limited to the exemplary embodiments corresponding to the reference signs/numerals.

What is claimed is:

1. A system, comprising:
   a first data storage element comprising a non-transitory computer readable storage medium storing a first set of data including patient images;
   wherein each patient image comprises pixel data and descriptive data;
   a second data storage element comprising a non-transitory computer readable storage medium storing a plurality of second sets of data, wherein each second set of data is derived from the first set of data, wherein the plurality of second sets of data are automatically derived by a component of the system;
   an extraction component comprising a processor wherein the extraction component extracts descriptive information from the first set of data, including at least one of the descriptive data and information derivable directly from the patient images, to create the plurality of second sets of data;
   wherein each second set of data excludes the pixel data and comprises a searchable index of descriptive information in accordance with predefined parameters and wherein each searchable index comprises different descriptive information from the other searchable indexes; and
   a search element comprising the processor and a user interface, wherein the search element:
     sends a query to the second data storage element, the query comprising a string of text containing at least one attribute relating to at least one patient image, and
     receives a response comprising a reference to each patient image stored on the first data storage element possessing the at least one attribute.

2. The system of claim 1, wherein the extraction component performs the extraction on the first set of data to update the plurality of second sets of data upon the occurrence of a triggering event.

3. The system of claim 1, wherein the first data storage element stores patient images in a digital imaging and communications in medicine (DICOM) data format.

4. The system of claim 1, wherein the first data storage element is a Picture Archiving and Communication Systems (PACS).

5. The system of claim 1, further comprising: a retrieval element comprising the processor, wherein the retrieval element retrieves the first set of data from the first data storage element for processing by the extraction element.

6. The system of claim 5, wherein the retrieval element periodically retrieves new data including patient images from the first data storage element at regular intervals, wherein the new data is data added to the first data storage element since the previous retrieval of patient images.

7. The system of claim 1, wherein the string of text contains a plurality of attributes relating to the at least one patient image.

8. The system of claim 1, wherein the response to the query comprises a reference to each of a plurality of patient images.

9. The system of claim 1, wherein the predefined parameters are existing indices based on medical knowledge for optimizing the plurality of second sets of data.

10. A method, comprising:
    storing a first set of data including patient images;
    wherein each patient image comprises pixel data and descriptive data;
    extracting, with a processor, descriptive information from the first set of data to create a plurality of second sets of data, wherein the plurality of the second sets of data are automatically created by a component of a system configured to perform the method;
    wherein the descriptive information includes at least one of the descriptive data and data derivable directly from the patient images;

wherein each second set of data excludes the pixel data and comprises a searchable index of the descriptive information in accordance with predefined parameters and wherein each searchable index comprises different descriptive information from the other searchable indexes;

storing the plurality of second sets of data;

sending, by the processor and user interface, a query to the second data storage element, the query comprising a string of text containing at least one attribute relating to at least one patient image; and receiving, by the user interface, a response comprising a reference to each patient image stored on the first data storage element possessing the at least one attribute.

11. The method of claim 10, further comprising: periodically performing the extracting from the first set of data at regular intervals to update the plurality of second sets of data.

12. The method of claim 10, further comprising: receiving a search term that is unrelated to a patient identifier; and returning an entry of one of the plurality of second sets of data corresponding to the search term.

13. The method of claim 10, wherein the first set of data stores data in a digital imaging and communications in medicine (DICOM) format.

14. The method of claim 10, wherein the plurality of second sets of data are stored in one of a spreadsheet and a database.

15. The method of claim 10, wherein the first set of data is a Picture Archiving and Communication Systems (PACS).

16. A non-transitory computer readable storage medium including a set of instructions executable by a processor, the instructions operable to:

store a first set of data including patient images; wherein each patient image comprises pixel data and descriptive data;

extract, descriptive information from the first set of data, to create a plurality of second sets of data, wherein the processor automatically creates the plurality of second sets of data;

wherein the descriptive information includes at least one of the descriptive data and data derivable directly from the patient images;

wherein each second set of data excludes the pixel data and comprises a searchable index of the descriptive information in accordance with predefined parameters and wherein each searchable index comprises different descriptive information from the other searchable indexes;

store the plurality of second sets of data;

send, by a processor and user interface, a query to the second data storage element, the query comprising a string of text containing at least one attribute relating to at least one patient image; and receive, by the user interface, a response comprising a reference to each patient image stored on the first data storage element possessing the at least one attribute.

17. The storage medium of claim 16, wherein the instructions are further operable to: periodically perform the extracting of the first set of data at regular intervals to update the plurality of second sets of data.

18. The storage medium of claim 16, wherein the instructions are further operable to: receive a search term that is unrelated to a patient identifier; and return an entry of one of the plurality of second sets of data corresponding to the search term.

* * * * *